US00PP08252P

United States Patent [19]

Dehan

[11] Patent Number: Plant 8,252

[45] Date of Patent: Jun. 8, 1993

[54] IMPATIENS PLANT NAMED DANSHIR

[75] Inventor: Klara Dehan, Holon, Israel

[73] Assignee: Danziger —"Dan" Flower Farm, Moshav Mishmar Hashiva, Israel

[21] Appl. No.: 743,434

[22] Filed: Aug. 9, 1991

[51] Int. Cl.[5] ..... A01H 5/00
[52] U.S. Cl. ..... Plt./87.6
[58] Field of Search ..... Plt./87.6

*Primary Examiner*—James R. Feyrer
*Attorney, Agent, or Firm*—Foley & Lardner

[57] ABSTRACT

A distinct cultivar of Impatiens plant named Danshir, characterized by its medium size rose red bicolored flowers, very small dark green leaves, floriferous habit, very compact growth habit, and excellent branching.

1 Drawing Sheet

1

The present invention relates to a new and distinctive cultivar of Impatiens plant, botanically known as Impatiens, commercially known as New Guinea impatiens, and referred to by the cultivar name Danshir. The new cultivar was developed by me through controlled breeding by crossing the cultivar identified by the breeding No. 59-19B as the female parent with the cultivar identified as 39-13V as the male parent. Both parents are unreleased, proprietary lines.

Asexual reproduction of Danshir by cuttings taken by applicant at Mishmar Hashiva, Israel, has shown that the unique features of this new Impatiens are stabilized and are reproduced true to type in successive propagations. The cuttings preferably comprise tip cuttings with at least one axillary bud, which is vegetative and not a flower bud.

The following characteristics distinguish the new Impatiens from both its parent varieties and other cultivated Impatiens of this type known and used in the floriculture industry:

1. Medium size, rose red bicolored flowers. To the best knowledge of applicant, its flower color is unique.
2. Very small dark green leaves with red main vein.
3. Very floriferous blooming habit.
4. Very compact growth habit.
5. Excellent branching.

The accompanying color photographs illustrate the overall appearance of this cultivar, showing the colors as true as it is reasonably possible to obtain in a colored reproduction of this type. The photograph at the top of the sheet is a top perspective view of the flowers and foliage of a portion of a plant of Danshir. The photo at the bottom is an enlarged closeup of a single flower and surrounding foliage.

The new cultivar can be compared in certain characteristics to the cultivar Sesia. Both cultivars have a compact growth habit and small to medium flowers. The flower color of Danshir is a darker red, its leaves are slightly smaller than the leaves of Sesia, and there are differences in foliage color.

The following is a detailed description of my new Impatiens cultivar based on plants produced under commercial practice in Mishmar Hashiva, Israel. The description generally applies to growth conditions during both summer and winter, with only the growth rate and earlier flowering in summer distinguishing the different growing periods.

2

Color references are made to The Royal Horticultural Society Colour Chart except where general terms of ordinary dictionary significance are used.

Parentage:

*Male parent.*—39-13V.

*Female parent.*—59-b 19B.

Propagation:

A. *Type cutting.*—Tip cuttings with at least one axillary vegetative bud.

B. *Time to initiate roots.*—8–10 days both at 25°–30° C. summer, and 20°–22° C. winter.

C. *Rooting habit.*—Good root initiation.

Plant Description:

A. *Form.*—Mounded and symmetrical.

B. *Habit of growth.*—Compact with excellent branching and early flowering. The branches are red in color.

C. *Foliage description.*—(1) Size: Very small, approximately 6.0 cm in length and 2.5 cm in width. (2) Shape: Oval with acute tip. (3) Margin: Finely serrated. (4) Color: Young foliage top side 139A; underside closest to purple 79A but color not precisely shown in R.H.S. chart. Mature foliage top side 139A; underside 79A. (5) Venation: The main vein is red.

Flowering Description:

A. *Flowering habits.*—The flowers open vertically and require approximately 2–3 days from bud to open flower.

B. *Natural flowering season.*—Spring and summer in moderate climates. In Israel the cultivar will also flower in the winter. Flowering is continuous at temperatures above approximately 10° C. and with at least minimum levels of light.

C. *Flower buds.*—Typical. Spurs up to 4.5 cm long on mature buds with throat originating from major sepal; the wide, oval part of the spur is 1.0 cm by 0.8 cm and close to 59C in color; the long part is approximately 4.0 cm in length, almost straight, and green 145A in color.

D. *Flowers borne.*—Flower buds are presented at the tips of stems overlying the terminal whorls of leaves. It approximately two-three weeks from bud initiation until the flower opens. In each tip the initiation is at the same time, so when flowering commences there is a total inflorescence of about 30 flowers.

E. *Quantity of flowers.*—Very floriferous; flowering is continuous, with about 30–40 flowers being in bloom after 3 months in the summer.

F. *Petals.*—(1) Shape: Two pairs of petals heart shaped and a single petal differently shaped and without the indentation. (2) Color: Bicolor, main color 52B with showings of 50A and center approximately 53B-C, main color fades to 56A; under side 51A. (3) Number of petals: Five. (4) Size of flowers: 4–5 cm in diameter.

G. *Reproductive organs.*—(1) Stamens: One in number. (a) Anther color: Red. (b) Pollen color:

White. (2) Pistils: (a) Stigma: Cone shaped; green in color with red line. (b) Style: Green in color. (c) Ovaries: One in number; size 1.5 mm; color green.

Disease Resistance: Good to date.

Other Important Characteristics: Color of branches are red.

I claim:

1. A new and distinct cultivar of Impatiens named Danshir, as illustrated and described.

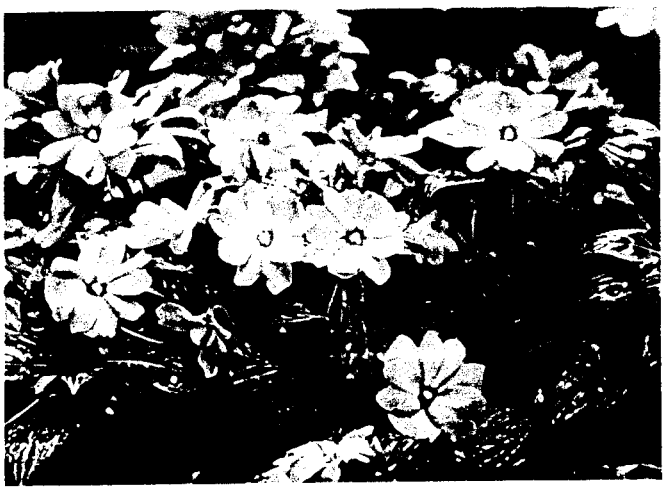
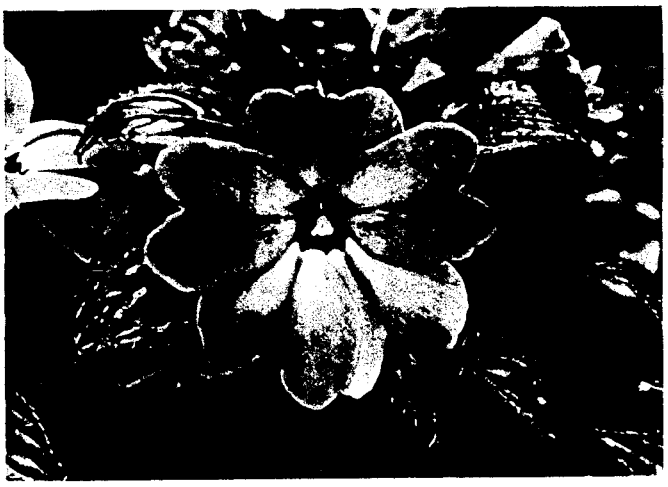

* * * * *